US008057438B2

(12) United States Patent
Bettuchi

(10) Patent No.: US 8,057,438 B2
(45) Date of Patent: Nov. 15, 2011

(54) SURGICAL SYSTEM HAVING A MAGNETIC ENTRY

(75) Inventor: Michael J. Bettuchi, Middletown, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 7 days.

(21) Appl. No.: 12/517,390

(22) PCT Filed: Jan. 3, 2008

(86) PCT No.: PCT/US2008/000162
§ 371 (c)(1),
(2), (4) Date: Jun. 3, 2009

(87) PCT Pub. No.: WO2008/085919
PCT Pub. Date: Jul. 17, 2008

(65) Prior Publication Data
US 2010/0010444 A1    Jan. 14, 2010

Related U.S. Application Data

(60) Provisional application No. 60/878,484, filed on Jan. 3, 2007.

(51) Int. Cl.
*A61M 5/178* (2006.01)
(52) U.S. Cl. .................................. 604/164.01
(58) Field of Classification Search ............. 604/164.01; 600/201–246
See application file for complete search history.

(56) References Cited

U.S. PATENT DOCUMENTS

| 2,949,931 | A | * | 8/1960 | Ruppright | 137/528 |
|---|---|---|---|---|---|
| 4,535,773 | A | * | 8/1985 | Yoon | 606/185 |
| 5,036,866 | A |  | 8/1991 | Eldrige, Jr. et al. |  |
| 5,423,761 | A | * | 6/1995 | Hein et al. | 604/167.01 |
| 5,573,545 | A | * | 11/1996 | Yoon | 606/185 |
| 7,780,639 | B2 | * | 8/2010 | Van Lue | 604/264 |
| 2006/0217666 | A1 | * | 9/2006 | Wenchell | 604/167.03 |
| 2009/0326466 | A1 | * | 12/2009 | Ross et al. | 604/167.01 |

FOREIGN PATENT DOCUMENTS

WO    WO 2005048814 A2 *  6/2005

OTHER PUBLICATIONS

International Search Report for PCT/US2008/000162—date of mailing is Jun. 11, 2008 (1 page).

* cited by examiner

*Primary Examiner* — Nicholas Lucchesi
*Assistant Examiner* — Jenna Zhang

(57) ABSTRACT

A surgical portal apparatus for receiving medical instrumentation includes a portal member adapted for passage through tissue for providing access to an underlying tissue site, and having a longitudinal opening extending therethrough. The portal member has a magnetic material for creating a magnetic field adapted to urge magnetically responsive instrumentation at least toward the longitudinal opening to permit passage therethrough and use of the instrumentation in performing a medical procedure adjacent the tissue site.

13 Claims, 2 Drawing Sheets

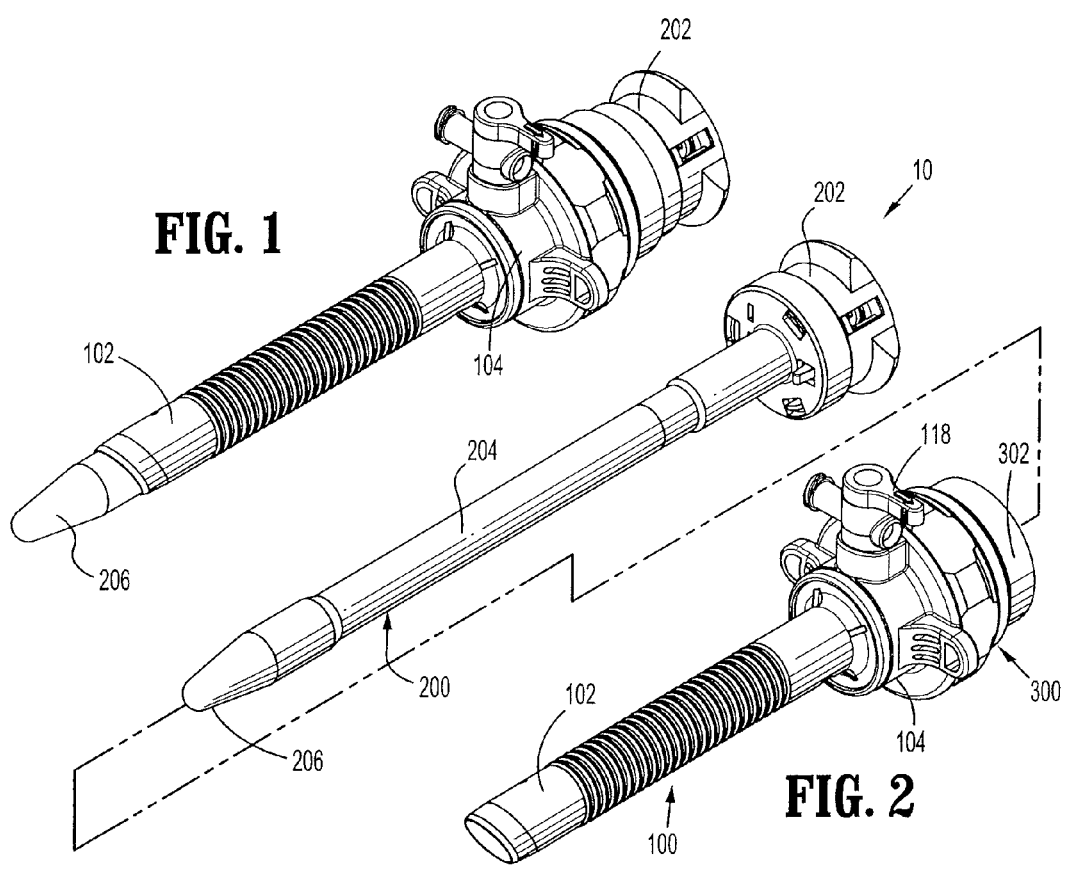

SURGICAL SYSTEM HAVING A MAGNETIC ENTRY

CROSS REFERENCE TO RELATED APPLICATIONS

This application is a National Stage Application of PCT/US2008/000162 filed Jan. 3, 2008 under 35 USC §371(a), which claims priority of U.S. Provisional Patent Application Ser. No. 60/878,484 filed Jan. 3, 2007 the entire contents of which are hereby incorporated by reference.

BACKGROUND

1. Field of the Disclosure

The present disclosure generally relates to surgical instruments for performing laparoscopic and endoscopic surgical procedures, and, more particularly, relates to a surgical trocar incorporating a novel magnetically active component for facilitating alignment and insertion of magnetically responsive surgical instruments during use in a surgical environment.

2. Description of the Related Art

In laparoscopic and endoscopic surgical procedures, a small incision or puncture is made in the patient's body to provide access for a surgical system which is inserted into the patient's body to permit viewing of the surgical site or for the insertion of instruments used in performing the surgical procedure. The surgical system may be in the form of a trocar cannula assembly incorporating an outer cannula and an obturator which is positioned in the outer cannula. The obturator includes a sharpened point or tip which is used create a path to the surgical site. The obturator is then removed leaving the cannula in place to maintain access to the surgical site. Once the cannula is in place, various surgical instruments such as graspers, scissors, dissectors, retractors or the like, may be inserted by a surgeon to perform the surgery. Typically, these surgical instruments are constructed from ferrous metals such as stainless steel, carbon steel, alloy steel or the like, and, thus, are inherently magnetically responsive.

SUMMARY

A surgical portal apparatus for receiving medical instrumentation includes a portal member adapted for passage through tissue for providing access to an underlying tissue site, and having a longitudinal opening extending therethrough. The portal member has a magnetic material for creating a magnetic field adapted to urge magnetically responsive instrumentation at least toward the longitudinal opening to permit passage therethrough and use of the instrumentation in performing a medical procedure adjacent the tissue site.

The portal member may include a housing and a sleeve extending from the housing with the magnetic material being disposed at least within the housing. The magnetic material may be at least partially disposed within an interior surface of the housing. The interior surface containing the magnetic material may at least partially define the longitudinal opening. The magnetic material may be coaxially arranged about the longitudinal axis. Preferably, the interior surface defines a tapered arrangement relative to the longitudinal axis.

Alternatively, the magnetic material is disposed within the sleeve. The portal member may include an electromagnet. The electromagnet may define a coiled arrangement.

In another embodiment, a surgical portal apparatus for receiving medical instrumentation includes a portal member adapted for passage through tissue for providing access to an underlying tissue site. The portal member includes a portal housing and a portal sleeve extending distally from the portal housing. The portal sleeve defines a longitudinal axis and has a longitudinal opening extending through the proximal and distal ends. The portal housing is adapted to establish a magnetic field to urge magnetically responsive instrumentation at least toward the longitudinal opening to permit passage therethrough and use of the instrumentation in performing a medical procedure adjacent the tissue site. The portal member also may be adapted to establish a second magnetic field distal of the first magnetic field to facilitate advancement of the instrumentation through the portal member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein: said FIG. 1 is a perspective view of a surgical trocar assembly in accordance with the principles of the present disclosure including a cannula and an obturator assembled within the cannula;

FIG. 2 is a perspective view of the surgical trocar assembly of FIG. 1 illustrating the cannula and the obturator removed from the cannula.

DETAILED DESCRIPTION

Figure 3:
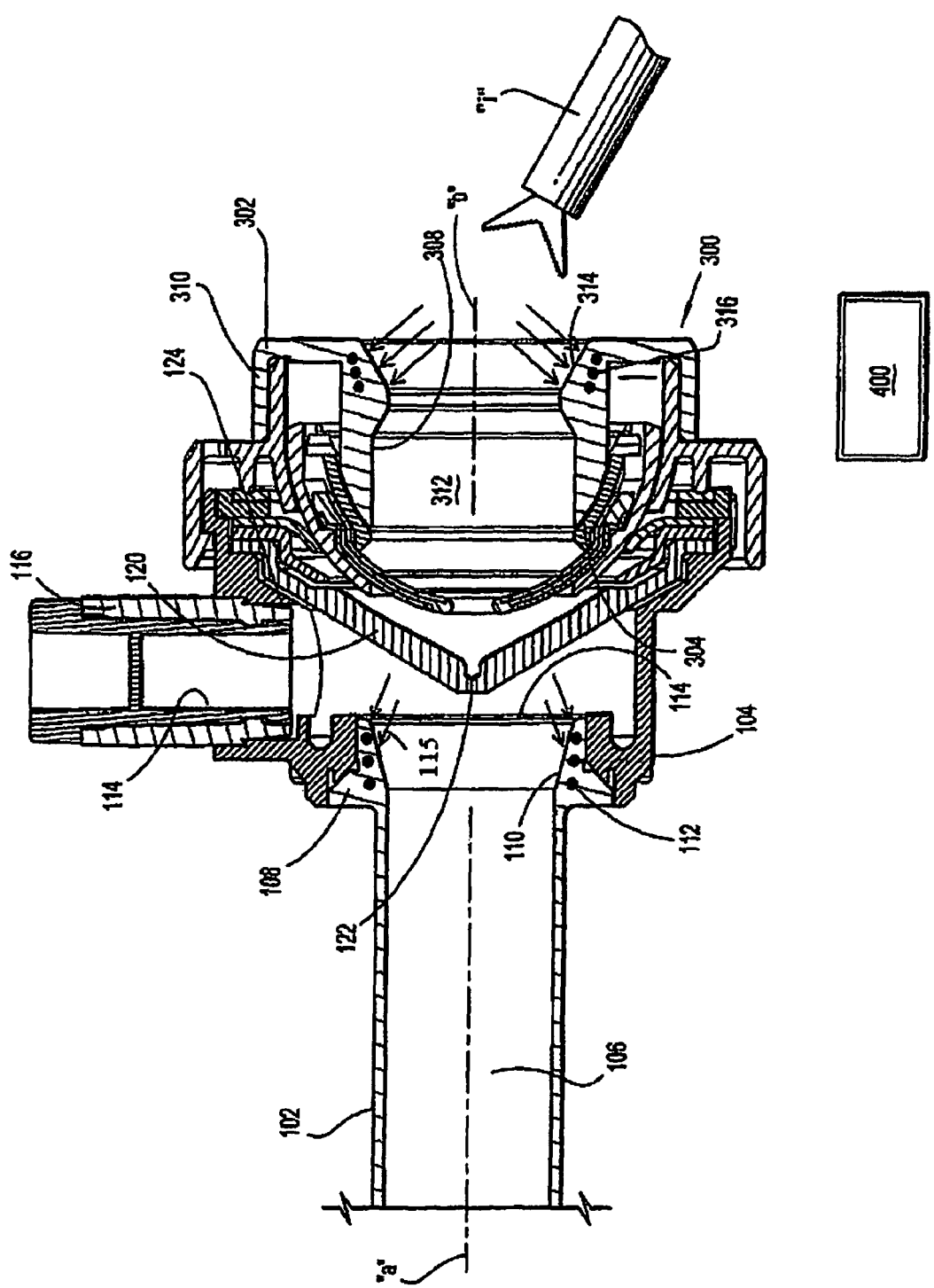
FIG. 3 is a side cross-sectional view of the cannula of the surgical trocar assembly of FIG. 1.

The portal apparatus contemplates the introduction and manipulation of various types of instrumentation. Examples of instrumentation include clip appliers, graspers, dissectors, retractors, staplers, laser probes, photographic devices, endoscopes and laparoscopes, tubes and the like. Such instruments will be collectively referred to herein as "instruments or instrumentation". In many instances, these instruments incorporate ferromagnetic material such as stainless steel and titanium, particularly, within the end effector area, which would inherently cause at least the end effector area of the respective instrument to be attracted to magnetically charged elements. In this regard, and in accordance with the present disclosure, the portal apparatus incorporates a magnetically charged material or portion which may facilitate introduction and/or advancement of the instrument within and through the portal apparatus.

In the following description, as is traditional, the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-2 illustrate the portal apparatus 10 of the present disclosure. Portal apparatus 10 may be in the form of a trocar assembly including cannula assembly 100 and obturator assembly 200 which is positionable within the cannula assembly 100. For example, in one embodiment, portal apparatus 10 is a laparoscopic trocar assembly particularly adapted for use in laparoscopic surgery where the peritoneal cavity is insulated with a suitable gas, e.g., $CO_2$, to raise the cavity wall from the internal organs therein. Specifically, cannula assembly 100 with obturator assembly 200 positioned therein is applied against the body cavity or abdominal wall. Once obturator assembly 200 penetrates through the abdominal wall, the obturator assembly 200 is removed from the cannula assembly 100 to permit introduction of surgical instrumentation through the remaining cannula assembly 100 to perform the procedure.

Referring now to FIGS. 1-2, in conjunction with FIG. 3, cannula assembly 100 includes cannula sleeve 102 and cannula housing 104 mounted to an end of the sleeve 102. Any means for mounting cannula sleeve 102 to cannula housing 104 are envisioned including threaded arrangements, bayonet coupling, snap-fit arrangements, adhesives, etc. Cannula sleeve 102 and cannula housing 104 may be integrally formed. Cannula sleeve 102 defines a longitudinal axis "a" extending along the length of sleeve 102. Sleeve 102 further defines an internal longitudinal passage 106 dimensioned to permit passage of surgical instrumentation. Sleeve 102 defines collar 108 which is mounted to cannula housing 102 and an inner tapered wall 110 adjacent the collar 108. The sloped configuration of tapered wall 110 may assist in guiding the inserted instrument into longitudinal passage 106. Sleeve 102 may be formed of stainless steel or other rigid materials such as a polymeric material or the like. Sleeve 102 may be clear or opaque. The diameter of sleeve 102 may vary, but, typically ranges from about 10 mm to about 15 mm.

Cannula housing 104 includes port opening 114 and luer fitting 116 positioned within the port opening 114. Luer fitting 116 is adapted for connection to a supply of insufflation gaseous is conventional in the art and incorporates valve 118 (FIGS. 1-2) to selectively open and close the passage of the luer fitting 116. Cannula housing 104 further includes duckbill or zero closure valve 120 which tapers distally and inwardly to a sealed configuration. Closure valve 120 defines slit 122 which opens to permit passage of the surgical instrumentation and closes in the absence of the instrumentation. Closure valve 120 is preferably adapted to close upon exposure to the forces exerted by the insufflation gases in the internal cavity. Other zero closure valves are also contemplated including single or multiple slit valve arrangements, trumpet valves, flapper valves, etc. Closure valve 120 rests upon internal shelf 124 of cannula housing 104 when assembled.

Obturator assembly 200 includes obturator housing 202 and elongated obturator 204 extending from the obturator housing 202. Elongated obturator 204 may include penetrating tip 206 dimensioned to pierce, penetrate or incise tissue. Penetrating tip 206 may be bladed, pyramidal in shape or blunt.

Portal apparatus 10 may also incorporate seal assembly 300. Seal assembly 300 may be a separate component from cannula assembly 100 and, accordingly, adapted for releasable connection to the cannula assembly 100. Alternatively, seal assembly 300 may be incorporated as part of cannula assembly 100. Seal assembly 300 includes a seal housing, generally identified as reference numeral 302, and gimbal mount 304 which is disposed within the seal housing 302. Seal housing 302 houses the sealing components of the assembly and defines the outer valve or seal body of the seal assembly 300. Seal housing 302 defines central seal housing axis "b" which is preferably parallel to the axis "a" of cannula sleeve 302 and, more specifically, coincident with the axis "a" of the cannula sleeve 302. Seal housing 302 may incorporate multiple housing components, or may be a single unit.

Seal housing 302 defines inner guide wall 308 and outer wall 310 disposed radially outwardly of the inner guide wall 308. Inner guide wall 308 defines central passage 312 which is dimensioned to receive a surgical instrument and laterally confine the instrument within seal housing 302. Inner guide wall 308 defines sloped or tapered portion 314 adjacent its proximal end. Sloped portion 314 is obliquely arranged relative to seal housing axis "b" and extends radially inwardly relative to the seal housing axis "b" in the distal direction. Sloped portion 314 assists in guiding the inserted instrument into central passage 312, particularly, when the instrument is non-aligned or off-axis relative to the seal housing axis "b", or introduced at an angle relative to the seal housing axis "b". Sloped portion 314 provides more flexibility to the surgeon by removing the necessity that the instrument be substantially aligned with the seal housing axis "b" upon insertion.

Gimbal mount 304 is mounted in a manner to permit angulation and/or rotational movement of the gimbal mount 104 relative to, or about, seal housing axis "b". Specifically, gimbal mount 304 is free to angulate relative to seal housing axis "b" through a range of motion within seal housing 302. Further details of gimbal mount 104 may be ascertained by reference to commonly assigned U.S. Patent Publication No. 2006/0224120 to Smith, the entire contents of which are incorporated herein by reference.

Referring now to FIG. 3, the aspects of the ferromagnetic capabilities of trocar assembly 10 and the features provided thereby in guiding and facilitating introduction and passage of instrumentation will be discussed. In one embodiment, seal housing 302 includes magnetically active member 316 adjacent sloped portion 314 to attract a magnetically responsive object such as, for example, the tip of a medical instrument "i." In one embodiment, magnetically active member 316 is a coiled or annular arrangement disposed on the surface of sloped portion 314 or embedded therewithin, and extending a predetermined distance along the seal axis "b". The annular arrangement of magnetically active member 316 provides a magnetic force (indicated by arrows 318) which is sufficient to urge a magnetically responsive object, such as, for example, the tip of medical instrument "i", in general alignment with axes "a" and "b", into central passage 312 and distally along the longitudinal axis "a". In this manner, a surgeon need only position medical instrument "i" within the proximity of central passage 312. Thereafter, surgical instrument "i" is aligned via the magnetic forces 318 and advanced through central passage 312 and cannula sleeve 102. Moreover, the surgeon may advance surgical instrument "i" through cannula assembly 200 with one hand without having to steady cannula assembly 200 with the other hand as is typically necessary to facilitate alignment of instrumentation with the passageway to the surgical site.

As a further alternative, cannula assembly 100 may include a second magnetically active member distal of the first mentioned magnetically active member 316. In one embodiment, collar 108 of cannula sleeve 102 incorporates magnetically active member 112 disposed on the surface or embedded within the collar 108. Magnetically active member 112 defines a magnetic field creating a magnetic force (as indicated by directional arrows 115) along the longitudinal axis "a" in a general distal direction. This magnetic field assists in attracting and passing the instrument "i" along the longitudinal axis "b" through sleeve 102 and also into central alignment with the longitudinal axis "a". It is envisioned that magnetically active member 112 may be embedded within cannula housing 104.

Magnetically active members 112, 316 may incorporate any magnetic material suitable for the intended purpose of attracting a ferromagnetic material of the instrument "i" as appreciated by one skilled in the art. Magnetically active members 112, 316 may be in the form of a permanent magnet or may be an electromagnet. In the embodiment incorporating an electromagnetic, an electromagnetic generator 400 is provided and in electrical communication with the magnetically active members 112, 316 to create the respective magnetic field on demand.

In use, an instrument is positioned adjacent the portal apparatus 10 and advanced through cannula sleeve 102 as facilitated by either or both magnetically active members 112, 316 as discussed hereinabove. The instrument "i" may be used to perform a desired procedure. When the instrument "i" is not in use, the clinician may, in one embodiment, release the instrument "i". The released instrument "i" may remain unattended within cannula sleeve 102, i.e., be retained with the cannula sleeve 102, through the created magnetic fields.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical portal apparatus for receiving medical instrumentation, which comprises:
   a portal member adapted for passage through tissue for providing access to an underlying tissue site, the portal member defining a longitudinal axis, and proximal and distal ends, the portal member including a portal housing and a portal sleeve extending distally from the portal housing, the portal member having a longitudinal opening extending through the proximal and distal ends, the portal housing having a first magnetic material for creating a first magnetic field, and the portal sleeve having a second magnetic material for creating a second magnetic field, the first and second magnetic fields each adapted to urge magnetically responsive instrumentation with respect to the longitudinal axis, at least one of the first and second magnetic materials having a coiled arrangement that defines a radial dimension decreasing in a distal direction.

2. The surgical portal apparatus according to claim 1 wherein the first magnetic material is at least partially disposed within an interior surface of the portal housing.

3. The surgical portal apparatus according to claim 2 wherein the interior surface containing the first magnetic material at least partially defines the longitudinal opening.

4. The surgical portal apparatus according to claim 3 wherein the first magnetic material is coaxially arranged about the longitudinal axis.

5. The surgical portal apparatus according to claim 4 wherein the interior surface defines a tapered arrangement relative to the longitudinal axis.

6. The surgical portal apparatus according to claim 1 wherein at least one of the first and second magnetic materials is an electromagnet.

7. The surgical portal apparatus according to claim 6 wherein the electromagnet defines a coiled arrangement.

8. The surgical portal apparatus according to claim 1, wherein at least one of the first and second magnetic materials is disposed such that the at least one of the first and second magnetic materials creates a magnetic field that urges magnetically responsive instrumentation toward the longitudinal opening.

9. The surgical portal apparatus according to claim 1, wherein at least one of the first and second magnetic materials is disposed such that the at least one of the first and second magnetic materials creates a magnetic field that urges magnetically responsive instrumentation to pass the longitudinal opening in a substantially aligned relation with respect to the longitudinal axis.

10. The surgical portal apparatus according to claim 1, wherein the first magnetic material and the second magnetic material each define a tapered configuration that tapers distally.

11. The surgical portal apparatus according to claim 1, wherein each of the first and second magnetic materials defines a coiled arrangement with a diameter decreasing in the distal direction.

12. A surgical portal apparatus for receiving medical instrumentation, which comprises:
   a portal member adapted for passage through tissue for providing access to an underlying tissue site, the portal member including a portal housing and a portal sleeve extending distally from the portal housing, the portal sleeve defining a longitudinal axis and having a longitudinal opening extending through the proximal and distal ends, the portal housing having a first magnetic material for creating a first magnetic field, the portal sleeve having a second magnetic material for creating a second magnetic field, at least one of the first and second magnetic materials having an annular arrangement that defines a radial dimension decreasing in a distal direction.

13. The surgical portal apparatus according to claim 12, wherein each of the first and second magnetic materials defines an annular arrangement with a diameter decreasing in the distal direction.

* * * * *